United States Patent
Pumm et al.

(10) Patent No.: US 9,168,556 B2
(45) Date of Patent: Oct. 27, 2015

(54) MEMBRANE NEBULIZER AND METHOD FOR WELDING A MEMBRANE TO A CARRIER DURING THE PRODUCTION OF A MEMBRANE NEBULIZER

(75) Inventors: Gerhard Pumm, Oberau (DE); René Seifert, Murnau (DE); Philipp Holzmann, München (DE); Nicole Brune, Germering (DE)

(73) Assignee: PARI Pharma GmbH, Starnberg (DE)

( * ) Notice: Subject to any disclaimer, the term of this patent is extended or adjusted under 35 U.S.C. 154(b) by 822 days.

(21) Appl. No.: 13/375,818

(22) PCT Filed: Jun. 2, 2010

(86) PCT No.: PCT/EP2010/057718
§ 371 (c)(1),
(2), (4) Date: Mar. 13, 2012

(87) PCT Pub. No.: WO2010/139730
PCT Pub. Date: Dec. 9, 2010

(65) Prior Publication Data
US 2012/0167877 A1     Jul. 5, 2012

(30) Foreign Application Priority Data
Jun. 2, 2009   (DE) .................. 10 2009 026 636

(51) Int. Cl.
| A61M 11/00 | (2006.01) |
| B05B 17/00 | (2006.01) |
| A61M 15/00 | (2006.01) |
| B05B 17/06 | (2006.01) |
| B23K 11/00 | (2006.01) |
| B23K 11/093 | (2006.01) |
| B23K 11/22 | (2006.01) |

(52) U.S. Cl.
CPC .......... *B05B 17/0646* (2013.01); *A61M 11/005* (2013.01); *A61M 15/0085* (2013.01); *B05B 17/0661* (2013.01); *B23K 11/0026* (2013.01);
(Continued)

(58) Field of Classification Search
CPC . A61M 15/009; A61M 11/005; A61M 11/06; A61M 15/085; A61M 11/00
USPC ....................................... 128/200.14–200.22
See application file for complete search history.

(56) References Cited

U.S. PATENT DOCUMENTS

| 4,420,848 A | 12/1983 | Becker |
| 6,689,981 B1 | 2/2004 | Ananthanarayanan et al. |

(Continued)

FOREIGN PATENT DOCUMENTS

| DE | 36 89 497 T2 | 3/1987 |
| DE | 101 22 065 A1 | 12/2002 |

(Continued)

OTHER PUBLICATIONS

Translation of the International Preliminary Report on Patentability dated Aug. 8, 2011 from corresponding International Application No. PCT/EP2010/057718.

*Primary Examiner* — Steven Douglas
(74) *Attorney, Agent, or Firm* — Wolf, Greenfield & Sacks, P.C.

(57) ABSTRACT

A membrane nebulizer for producing aerosol in an aerosol therapy device includes a membrane having several through-holes for nebulizing a fluid; and a laminar carrier having an opening, the membrane being arranged in the opening and fastened to the carrier in such a way that the nebulizing occurs on a first side of the carrier and the fluid is present at the membrane on the opposite second side of the carrier, wherein the membrane is welded to the carrier by means of a resistance welding method.

13 Claims, 1 Drawing Sheet

(52) U.S. Cl.
CPC ............... *B23K 11/093* (2013.01); *B23K 11/22* (2013.01); *B23K 2201/36* (2013.01); *B23K 2203/02* (2013.01); *B23K 2203/10* (2013.01)

(56) References Cited

U.S. PATENT DOCUMENTS

| | | |
|---|---|---|
| 2005/0236821 A1 | 10/2005 | Hofmann et al. |
| 2006/0207591 A1 | 9/2006 | Gallem et al. |
| 2008/0308096 A1 | 12/2008 | Borgschulte et al. |

FOREIGN PATENT DOCUMENTS

| | | |
|---|---|---|
| DE | 20 2004 001 803 U1 | 7/2004 |
| DE | 10 2005 006 375 A1 | 8/2006 |
| EP | 0 212 255 B1 | 3/1987 |
| EP | 1 386 672 A1 | 2/2004 |
| WO | WO 01/76762 A2 | 10/2001 |
| WO | WO 2006/127181 A2 | 11/2006 |

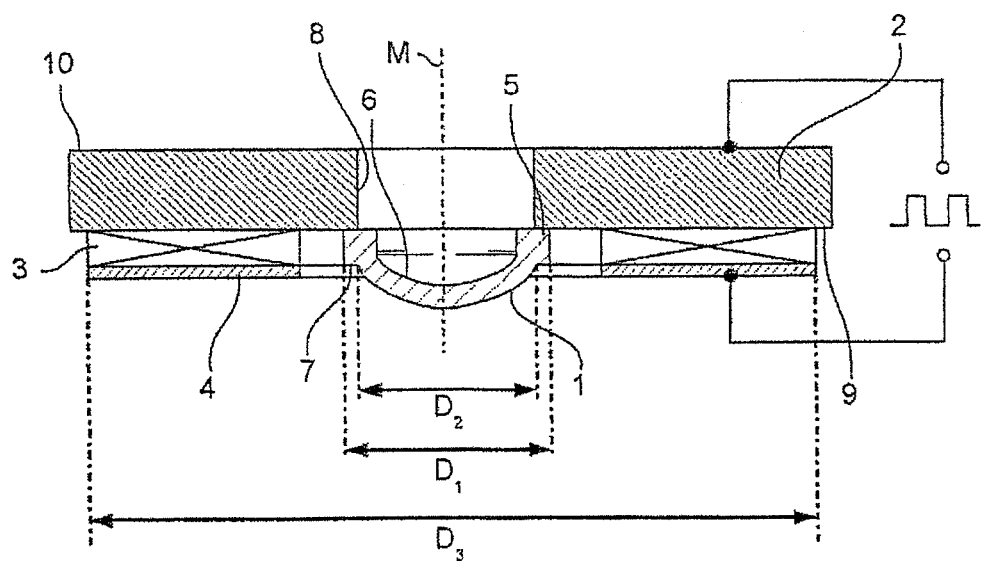

MEMBRANE NEBULIZER AND METHOD FOR WELDING A MEMBRANE TO A CARRIER DURING THE PRODUCTION OF A MEMBRANE NEBULIZER

FIELD OF THE INVENTION

The present invention relates to a membrane nebuliser for generating liquid droplets using an oscillating membrane, in particular for nebulising fluids, in particular liquids for therapeutic purposes. In other words, the present invention relates to a membrane nebuliser for generating an aerosol in an aerosol therapy device. Furthermore, the present invention also relates to a method for connecting a membrane to a planar carrier during the production of such a membrane nebuliser.

DESCRIPTION OF RELATED ART

A membrane nebuliser is known, for example, from DE 101 22 065 A1 or DE 10 2005 006 375 A1.

During the production of such a membrane nebuliser, the membrane must be connected to the actuator that causes the membrane to oscillate, in particular a piezo oscillator. This connection is presently realised by gluing the membrane to the carrier using an adhesive. A disadvantage of this is, on the one hand, the long processing time which is due primarily to the hardening time of the adhesive. Furthermore, the use of adhesives fundamentally involves a difficult handling, such as special pressing tools, in a continuous production process. It is also problematic to find a suitable adhesive since the adhesive must be medically approved and must be capable of being repeatedly autoclaved (the current minimum requirement is 50 cycles). The carrier and the membrane must additionally be treated in advance, for example sandblasted and purified, in order to improve adhesion via the adhesive.

SUMMARY

The object of the present invention is therefore to create a membrane nebuliser which, whilst maintaining the same oscillation behaviour of the membrane and thus the same aerosol generation, can be produced in a simpler, quicker and thus more cost-effective manner, as well as to propose a method for connecting a membrane to a carrier during the production of a membrane nebuliser, which is simpler, quicker and more cost-effective than the present adhesive method.

This object is achieved by a membrane nebuliser, a method and a use as shown and described herein.

One problem in achieving this object is that the type of connection between the membrane and the carrier (or to the actuator, in particular the piezo oscillator) has a significant influence on the oscillation behaviour and thus on the aerosol generation of the membrane. All of the metal components, including the actuator, together form a flexural oscillator having a characteristic oscillatory behaviour. This includes typical amplitudes, resonances and power conversion, which are realised depending on the setting of the units and production. Furthermore, a sealed and completely closed, for instance annular, connection must be formed in the region where the membrane connects to the carrier since otherwise uncontrolled fluid, in particular the escape of medicament, may occur during nebulisation. Finally, in particular the membrane but also the carrier are very thin metal components having a thickness in the range of 25 µm or 500 µm, respectively (the wall thickness of the membrane is in the range of between 25 µm and 200 µm and the wall thickness of the carrier is in the range of between 50 µm and 500 µm). Therefore, connection methods having high heat production can, in principle, be ruled out since owing to the production of heat, a distortion or lack of sealing (leakage) between the two components to be connected is to be expected, as is thus a significant influence on the oscillation behaviour and aerosol generation.

However, it has surprisingly emerged that welding of the membrane to the carrier using a resistance welding method is possible with such a low distortion of the components that the oscillation behaviour and aerosol generation are not influenced or at least remain manageable. The idea forming the basis for the present invention is therefore to weld the membrane and the planar carrier of a membrane nebuliser together, thereby using in particular a resistance welding method.

According to the present invention, a membrane nebuliser for generating an aerosol in an aerosol therapy device or for generating liquid droplets comprises a membrane having a plurality of through-holes for nebulising a fluid. An actuator, in particular a piezo oscillator, which causes the membrane to oscillate, may be provided for this purpose, and thus the fluid is nebulised through the through-holes from one side to the other. As regards this mode of function, reference is made to DE 101 22 065 A1 for further details. A planar carrier which comprises a (preferably circular) opening is furthermore provided, the membrane being arranged in the opening or being arranged over the opening and being attached to the carrier such that the fluid can be present on one side of the membrane, whilst it is nebulised on the opposite side of the membrane. For this purpose, the membrane is arranged in the opening and attached to the carrier in such a manner that nebulisation takes place on a first side of the carrier and the fluid is present on the membrane on the opposite second side of the carrier. The present invention is characterised in that the membrane is welded around its entire circumference to the carrier. A resistance welding method is preferably used for this purpose. Medium frequency welding and capacitor discharge welding may, for example, be used here. By using resistance welding, reproducible welding results are achieved whilst at the same time minimising production costs and thus increasing cost-effectiveness. Further advantages are minimised connection costs owing to low connected loads as well as low energy costs owing to an optimal power factor.

In medium frequency welding, the required energy for the welding processes is supplied in a regulated manner with almost any pulse progression by means of modern inverter power sources. The supply voltage is first of all rectified in the inverter and is then provided as a pulsed DC voltage via a regulated converter and a transformer. Medium frequency welding is used for various materials such as aluminium, stainless steel and coated steel sheets. It is thereby also possible to connect materials having a different heat conductivity, such as aluminium to steel.

In capacitor discharge welding, the energy required for welding is switched from a previously charged capacitor bank to one or more welding electrodes. Owing to the rapid discharge of the energy stored in the capacitors, the current in the secondary circuit increases very rapidly, as a result of which the temperature at the welding site can also increase just as rapidly. This rapid temperature increase heats the welding zone before the heat can dissipate, thus preventing a heating of the regions around the welding site or the welding area. As a result, a short welding time with a low energy requirement can be achieved. Owing to the low heat input, a stable process and an accurate welding area are furthermore achieved, and the distortion of the very thin components is kept at an acceptable or manageable level.

Furthermore, this connection method advantageously creates the possibility to bring the membrane into surface contact with the first side of the carrier, i.e. that side of the carrier on which nebulisation occurs. This has the advantage as compared to bringing it into contact with the second side that the oscillation behaviour of the entire component (flexural oscillator) is positively influenced in the desired case of use. In addition, assembly of the component from one side is possible. However, a connection on both sides is generally conceivable depending on the desired optimisation. A liquid-tight (sealed) connection form is therefore achieved, which is mechanically and electrically stable and can be reproduced within certain tolerance limits.

An advantage of capacitor discharge welding as compared to medium frequency welding proved to be the lower required electric power supply. In the case of medium frequency welding a current of approximately 300 to 500 A is required whereas in the case of capacitor discharge welding currents of up to 64 A are sufficient. Both methods are generally suitable for this use.

The advantage of these resistance welding methods is direct quality control by means of the measured resistances and currents. This enables an in-process control and saves on further quality control measurements. For example, the sealing cannot be directly measured in the alternative of laser welding, and a separate camera control measurement, for example, would be necessary.

The membrane thereby preferably has an effective area which may be, for example, circular and in which the through-holes are arranged, as well as a preferably annular fixing area for fixation to the carrier, which surrounds the effective area around its entire circumference. The fixing area is configured as a collar which is in surface contact with the carrier. As mentioned above, it is thereby preferred for the collar to be in surface contact with the first side of the carrier and for the effective area to preferably be centred relative to the opening of the carrier. The opening may likewise be, for example, circular and the effective area may be arranged concentric to the opening.

As compared to an adhesive connection and owing to the strength (stability) of the welding connection and the achievable sealing, the collar which is in surface contact with the carrier can, as a result of the present invention, be configured with a very small area that is preferably less than 96 $mm^2$, preferred less than 80 $mm^2$, more preferred less than 40 $mm^2$ and most preferred less than 20 $mm^2$. However, the area is preferably ≥5 $mm^2$ and most preferred greater than or equal to 10 $mm^2$. This leads on the one hand to the material consumption being reduced and the weld seam being optimised, and on the other hand to the desired oscillation behaviour of the components (more specifically of the flexural oscillator) being achieved in an advantageous manner.

As already stated above, the membrane and/or the carrier may be formed from stainless steel or another metallic material which is suitable and approved for medical use. The wall thickness of the membrane is thereby preferably less than 200 μm, preferred between 25 μm and 200 μm and most preferred between 50 μm and 120 μm. The wall thickness of the carrier is preferably less than 500 μm, preferred between 50 μm and 500 μm and most preferred between 100 μm and 400 μm.

Furthermore, as mentioned, an actuator may be provided to cause at least the membrane for nebulising the fluid to oscillate, whereby the actuator may form the carrier or may be connected, for example adhered, to the carrier. It may be arranged on the same side as the membrane or on the opposite second side of the carrier. Furthermore, the actuator is preferably a piezoceramic actuator, in particular a piezo oscillator. The wall thickness of the actuator is thereby of a comparable size and is preferably less than 500 μm, preferred between 25 μm and 500 μm and most preferred between 100 μm and 400 μm.

In addition to the aforementioned membrane nebuliser, the present invention also proposes an aerosol therapy device having such a membrane nebuliser.

The present invention furthermore relates to a method for connecting a membrane, in particular a membrane of the type as mentioned above, to a planar carrier, which is also described above, during the production of a membrane nebuliser of an aerosol therapy device. The method thereby comprises the steps of bringing the region (fixing area) of the membrane (for example the collar) which is to be welded to the carrier into surface contact with the carrier. The effective area of the membrane is thereby accordingly aligned relative to the opening in the carrier such that the effective area lies over or in the opening. In the case of a circular effective area and a circular opening, the two circles are arranged, for example, concentrically. The same also applies as regards the, for instance, annular collar. A welding electrode which has a closed cross-section, for example is annular, is then pressed into surface contact with the region (fixing area) in which the carrier and the membrane are to be welded, and a resistance welding process (such as a medium frequency welding process or a capacitor discharge welding process) is carried out to connect the membrane and the carrier. The, for example, annular welding electrode thereby has a defined internal and external diameter, which defines the radial width (thickness) of the likewise annular welding seam.

In order to prevent corrosion damage during the welding process, which can primarily occur owing to the subsequent contact with different solutions and cleaning steps, the welding process takes place in a protective gas atmosphere, for example in forming gases, preferably argon, adapted to the materials used in each case.

It furthermore cannot be guaranteed that the current flow will flow evenly through the components via the welding electrode, as a result of which welding errors and leaks may possibly occur. It hereby emerged that the projection welding methods which are common in practice and which normally generate an even welding image cannot be optimally used for the present material thicknesses. It is not possible to reproduce a clean edge (projection) in this use. In order to avoid this problem, the welding current is partially applied and this process is repeated once or more according to requirements or the use. For this purpose, the welding electrode and the laminate consisting of the membrane and the carrier are rotated relative to one another once the first resistance welding process (such as a medium frequency or capacitor discharge welding process) has been carried out, i.e. the laminate and the welding electrode are displaced relative to one another, whereby the relative rotation should be less than 360°. A new welding process is then carried out. This displacement may be repeated several times, preferably three times, whereby the relative rotation is 120°, respectively. However, it is also conceivable to have several or even just two welding processes, with rotation preferably occurring at an equal spacing, for example 180° if welding is carried out twice or 90° if welding is carried out four times.

As mentioned above, it is advantageous for the stated reasons to bring the membrane into surface contact with the first side of the carrier in the region in which the membrane and the carrier are to be connected, i.e. on that side of the carrier on which nebulisation (or aerosol generation) takes place.

In addition to the method according to the invention, the present invention also proposes the use of a resistance welding method for welding a membrane of the type as described above, to a planar carrier, which is also described above, during the production of a membrane nebuliser.

Further advantages and features which can be implemented either alone or in combination with one or more of the above features are furthermore apparent from the following description of a preferred embodiment that is mentioned by way of an example, which is carried out with reference to the accompanying drawing.

BRIEF DESCRIPTION OF THE DRAWINGS

FIG. 1 is a cross-section of the membrane nebuliser of the present invention.

DETAILED DESCRIPTION

FIG. 1 shows a membrane nebuliser of the present invention. The oscillatable system shown in FIG. 1 is rotationally symmetrical relative to the central axis M indicated in FIG. 1. It comprises a curved membrane 1 and a carrier or substrate 2 having a centrally arranged circular opening 8. The curved membrane is arranged in the opening 8. The membrane 1 is also circular and arranged concentric to the central axis M. The membrane 1 comprises a circular, centrally arranged effective area which comprises a plurality of not visible through-holes in the size range of less than 10 μm and preferably between 1.5 μm and 5 μm in diameter. An annular collar 7 is arranged concentric to the effective area 6, said collar protruding over the opening 8 and serving to fix the membrane to the carrier 2. The carrier 2 has a first side 9 and an opposite or opposingly arranged side 10. When the membrane nebuliser is installed in an aerosol therapy device, the fluid to be nebulised is present on the side 10 and is thus above the opening 8 on the effective area 6 of the membrane 1. Nebulisation (or aerosol generation) occurs on the opposite side 9 when the shown system is caused to oscillate and the fluid, in particular a liquid, is nebulised through the plurality of through-holes (or exits as an aerosol) on the side 9. The carrier 2 is preferably also circular and has a diameter D3 of less than 30 mm, preferably less than 27 mm and particularly preferred of less than 24 mm. Furthermore, a piezo element 3 is attached, in particular adhered, to the carrier 2 on the same side 9, and an ac voltage can be applied via a first electrode 4 and via the carrier 2. The carrier 2 can thereby assume the function of a second electrode for the piezo element 3. However, a second electrode may also be provided on the side 10 of the carrier.

An ac voltage applied to the electrodes leads to a lengthening and shortening of the piezo element 3 in a direction perpendicular to the axis of symmetry M as shown in FIG. 1. As a result, during the alternating lengthening and shortening of the piezo element 3 the carrier is bent and is caused to flexurally oscillate, with these oscillations being transferred to membrane 1. The resonance frequencies of the oscillation system are determined on the one hand by the membrane 1, the substrate 2 and the piezo element 3 as well as by the type of fixing of the membrane 1 to the substrate 2. On the other hand, the resonance frequencies of the oscillation system are additionally influenced by the liquid which is supplied to the concave side of the membrane 1 and is present there during nebulisation. This is particularly true for therapeutic inhalation devices (for example medicament nebulisers), in which the liquid in a reservoir provided therefor is provided in sufficient amounts directly on the membrane.

The fixing of the membrane 1 to the carrier 2 takes place here by means of a welding seam 5 in the region of the collar 7. For this purpose, the collar 7 is in surface contact with the side 9 of the carrier 2. Connection is thereby carried out such that the membrane 1 with the collar 7 is brought into surface contact with the carrier or more specifically the side 9 of the carrier, and then an annular welding electrode (not shown) is pressed onto the surface of the collar 7 which is facing downwards in FIG. 1. The connection is then formed by means of a resistance welding process, preferably a capacitor discharge welding process. In order to achieve a sufficiently sealed connection, i.e. a completely closed welding seam 5 (annular welding seam) between the membrane 1 and the carrier 2, the laminate consisting of the membrane 1 and the carrier 2 is then, according to a preferred embodiment, rotated by 120° relative to the welding electrode or the welding electrode is rotated relative to the laminate, and the welding process is carried out again. A further rotation by 120° subsequently takes place, as does a further welding process. However, it goes without saying that just two welding processes or more than three welding processes may also be carried out.

The annular welding electrode is furthermore defined as regards its internal and external diameter so as to be able to adjust the width of the welding seam in the radial direction of the system. The width of the collar 7 is furthermore also accordingly adjusted in the radial direction. The area of the collar is thereby preferably in the range of between 5 mm$^2$ and a maximum of 96 mm$^2$, preferably a maximum of 80 mm$^2$, more preferred a maximum of 40 mm$^2$ and mostly preferred a maximum of 20 mm$^2$. The area is thereby measured in the region which protrudes over the opening 8, i.e. the region lying between the diameters D2 and D1 in FIG. 1.

In order to prevent corrosion, the aforementioned welding process is carried out in a protective gas atmosphere, for example in a specific atmosphere with forming gases and preferably argon, depending on which materials are being welded.

Owing to the present invention, the duration of the connection process can be significantly reduced, it is independent of third materials, i.e. adhesive, and does not require a pre-treatment of the materials. This connection furthermore has a higher strength and thus higher autoclaving resistance. The use of workpiece carriers for fixing the components during the adhesion process may furthermore be omitted, as a result of which the investment costs can be reduced whilst at the same time increasing the number of items.

It goes without saying that the above embodiment is only one example embodiment and that various different modifications are obvious to the person skilled in the art without deviating from the basic idea of the present invention, such as is apparent from the following claims. It is, for example, possible to attach the piezo element to the opposite side or to connect the membrane directly to the piezoelectric element. Furthermore, shapes other than the circular or annular elements arranged concentric to one another are conceivable. Materials other than the mentioned stainless steel may also be used for the membrane and the carrier. Accordingly, suitable protective gases must be used in each case. Actuators other than piezoelectric actuators may likewise also be used, such as, for example, shape memory alloys, oscillating pistons, pump motors, pump pistons, piezo motors, electromagnets with an oscillating core, relays or the like.

The invention claimed is:

1. A membrane nebuliser for generating an aerosol in an aerosol therapy device, comprising:
   a membrane comprising an effective area having a plurality of through-holes for nebulising a fluid and a fixing area surrounding the effective area around its circumference;
   a planar carrier having an opening, said membrane being arranged in the opening and fixed to the carrier in such a manner that nebulisation occurs on a first side of the carrier and the fluid is present on the membrane on the opposite second side of the carrier, wherein
   the membrane is bulged and the fixing area is configured as a collar in surface contact with a side of the carrier and welded around its circumference to the carrier by means of a resistance welding method; and
   a piezo element attached to a side of the carrier.

2. A membrane nebuliser according to claim 1, wherein the membrane is welded to the carrier by means of medium frequency welding or capacitor discharge welding.

3. A membrane nebuliser according to claim 1, wherein the collar which is in surface contact with the carrier has an area of less than 96 mm$^2$.

4. An aerosol therapy device having a membrane nebuliser according to claim 1.

5. A method for connecting a membrane and a planar carrier during manufacture of a membrane nebuliser of an aerosol therapy device, the membrane comprising an effective area, in which a plurality of through-holes for nebulizing a fluid are provided, and a collar for fixation to the carrier, which surrounds the effective area around its circumference, said method comprising the steps of:
   bringing a region of the collar of the membrane which is to be welded to the carrier into surface contact with said carrier;
   pressing a welding electrode having a closed cross section into surface contact with the collar; and
   resistance welding in the region of the collar so as to connect the membrane and the carrier.

6. A method according to claim 5, wherein the step of resistance welding, in particular medium frequency welding or capacitor discharge welding, takes place in a protective gas atmosphere.

7. A method according to claim 5, wherein following the step of resistance welding, the welding electrode and the laminate consisting of the membrane and the carrier are rotated relative to one another about an angle of less than 360° or the circle multiple (+/−360°), and the step of resistance welding is carried out again in the welding area, with this process preferably being repeated at least once.

8. A method according to claim 5, wherein the membrane in said region is brought into surface contact with that side of the carrier on which nebulisation takes place.

9. Method according to claim 5, further comprising the step of measuring resistances and/or currents during resistance welding for direct quality control.

10. A membrane nebuliser according to claim 1, wherein the collar which is in surface contact with the carrier has an area of less than 80 mm$^2$.

11. A membrane nebuliser according to claim 1, wherein the collar which is in surface contact with the carrier has an area of less than 40 mm$^2$.

12. A membrane nebuliser according to claim 1, wherein the collar which is in surface contact with the carrier has an area of less than 20 mm$^2$.

13. A membrane nebuliser according to claim 1, wherein the collar is in surface contact with the first side and the piezo element is attached to the first side.

* * * * *